United States Patent [19]
Bova et al.

[11] Patent Number: 5,189,687
[45] Date of Patent: * Feb. 23, 1993

[54] APPARATUS FOR STEREOTACTIC RADIOSURGERY

[75] Inventors: Frank J. Bova; William A. Friedman, both of Gainesville, Fla.

[73] Assignee: University of Florida Research Foundation, Inc., Alachua, Fla.

[ * ] Notice: The portion of the term of this patent subsequent to Jul. 2, 2008 has been disclaimed.

[21] Appl. No.: 709,812

[22] Filed: Jun. 4, 1991

Related U.S. Application Data

[63] Continuation of Ser. No. 353,816, May 18, 1989, Pat. No. 5,027,818.

[30] Foreign Application Priority Data

Dec. 2, 1988 [WO] PCT Int'l Appl. ... PCT/US88/04303

[51] Int. Cl.$^5$ .......................................... A61N 5/10
[52] U.S. Cl. ................................. 378/65; 378/4; 378/15; 378/68; 378/195; 378/208; 378/20
[58] Field of Search .............. 378/65.9, 68, 195, 205, 378/208, 17, 20, 4, 15

[56] References Cited

U.S. PATENT DOCUMENTS

| | | | |
|---|---|---|---|
| 2,181,620 | 11/1939 | Haupt . | |
| 2,638,554 | 5/1953 | Bartow et al. . | |
| 2,998,526 | 8/1961 | Green et al. . | |
| 3,766,384 | 10/1973 | Anderson | 378/209 |
| 3,777,124 | 12/1973 | Pavkovich | 378/65 |
| 3,987,281 | 10/1976 | Hodes | 378/65 |
| 3,991,310 | 11/1976 | Morrison | 378/65 |
| 4,008,400 | 2/1977 | Brunnett et al. | 378/4 |
| 4,117,337 | 9/1978 | Staats | 378/17 |
| 4,233,519 | 11/1980 | Coad | 378/65 |
| 4,341,220 | 7/1982 | Perry | 378/20 |
| 4,583,537 | 4/1986 | Derechinsky et al. | 606/130 |
| 4,598,208 | 7/1986 | Brunelli et al. . | |
| 4,608,977 | 9/1986 | Brown | 378/162 |
| 4,729,099 | 3/1988 | Iverson et al. | 364/413.26 |
| 4,780,898 | 10/1988 | Sundvist | 378/65 |
| 4,827,491 | 5/1989 | Barish | 378/65 |
| 4,885,998 | 12/1989 | Span et al. | 378/209 |
| 5,027,818 | 7/1991 | Bova et al. | 378/65 |

FOREIGN PATENT DOCUMENTS

| | | |
|---|---|---|
| 0075831 | 4/1983 | European Pat. Off. . |
| 0083756 | 10/1984 | European Pat. Off. . |
| 2014151 | 12/1971 | Fed. Rep. of Germany . |
| 2337859 | 2/1975 | Fed. Rep. of Germany . |
| 2385374 | 10/1978 | France . |
| 54-11999 | 5/1979 | Japan . |
| 59-64069 | 4/1984 | Japan . |
| 60-108065 | 6/1985 | Japan . |
| 60-185567 | 9/1985 | Japan . |

OTHER PUBLICATIONS

A System for Stereotactic Radiosurgery With a Linear Accelerator, Wendell Lutz, PH.D. et al., vol. 14, No. 2, Feb. 1988, pp. 373-381.

Primary Examiner—Janice A. Howell
Assistant Examiner—Kim-Kwok Chu
Attorney, Agent, or Firm—Kerkam, Stowell, Kondracki & Clarke

[57] ABSTRACT

Stereostactic radiosurgery apparatus for eliminating misalignments due to mechanical inaccuracies and sag of a linear accelerator radiation-emitting head which is swung through an arc comprises a guiding and support structure with a first bearing system for accurately rotating a collimator through a precise arc in a vertical plane with respect to a predetermined center point in the plane corresponding to a treatment location, a second gimbal bearing system for coupling the collimator to the head so that the rotating head can drive the collimator through its arc while mechanically uncoupling the head from the collimator by eliminating torques and forces on the collimator which would be exerted by mechanical inaccuracies or sag of the head, and a third bearing system for rotatably supporting a stereotactic floorstand for rotation about a vertical axis which intersects the center point. Since the movement of the collimator and the rotation of the floorstand are precisely controlled with respect to the center point, the apparatus ensures that radiation from the head will be accurately focused at the center point for all rotational positions of the head and floorstand. Mechanical linking arrangements are shown for allowing the floorstand to rotate automatically upon rotation of a patient treatment table. Although the linking arrangements are used to drive the rotation of the floorstand, the linkage arrangements prevent the introduction of positional inaccuracies in the floorstand rotation.

19 Claims, 8 Drawing Sheets

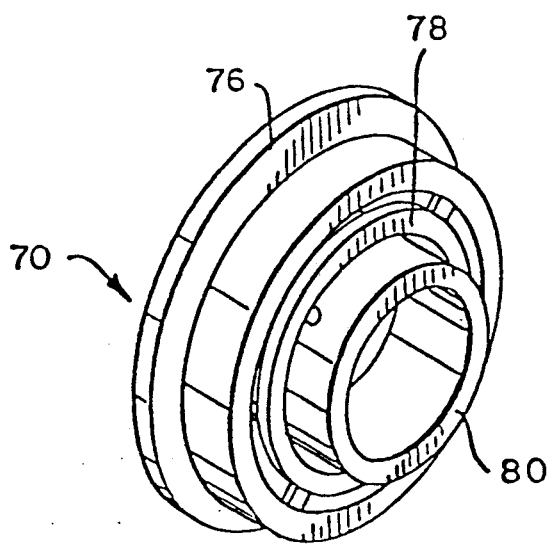
FIG. 8
FIG. 9
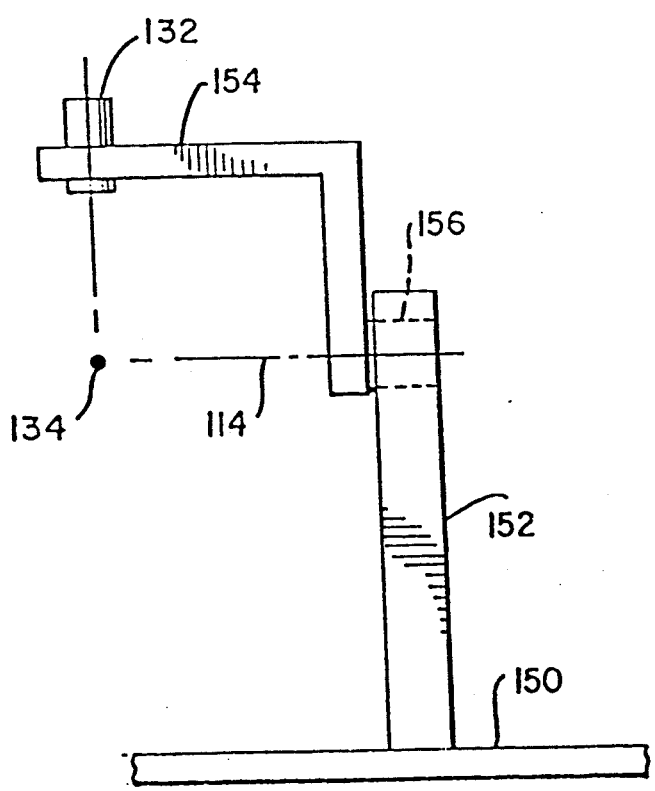
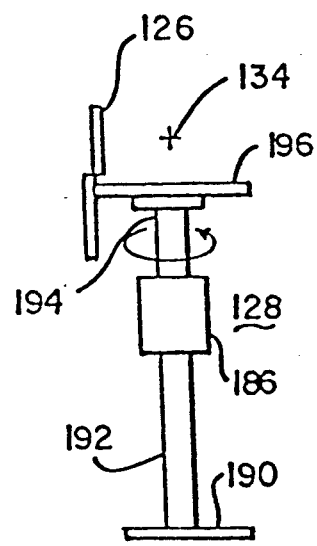
FIG. 10

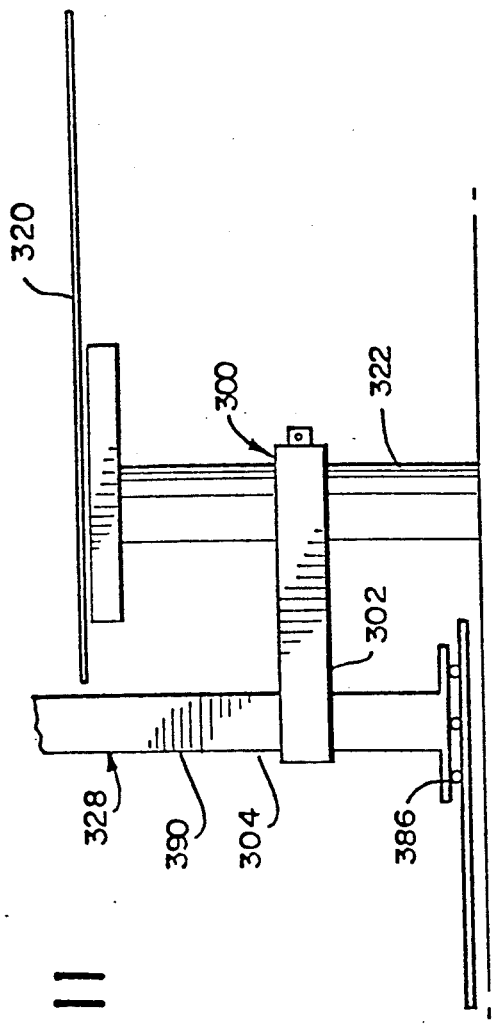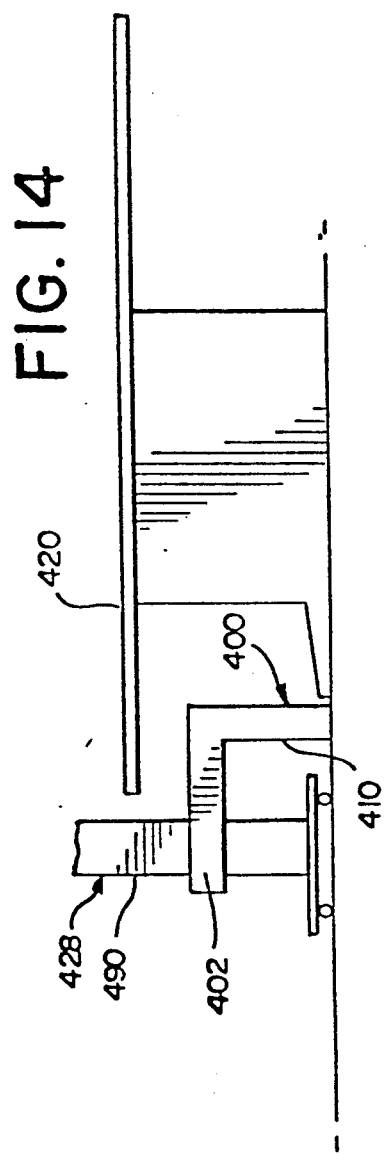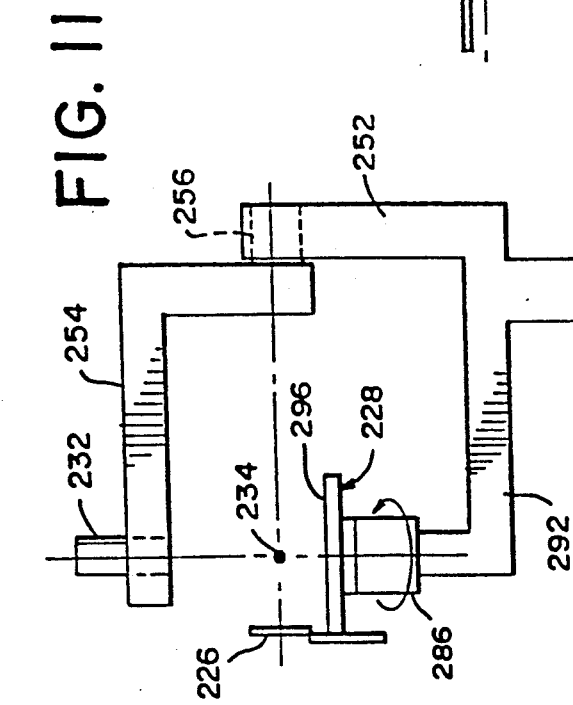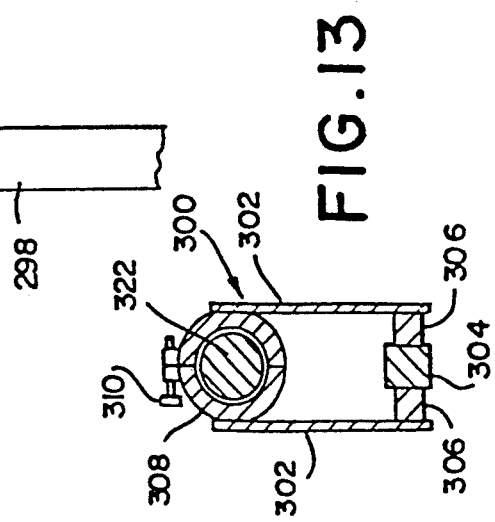

APPARATUS FOR STEREOTACTIC RADIOSURGERY

This is a continuation of application Ser. No. 353,816, now U.S. Pat. No. 5,027,818, filed May 18, 1989.

BACKGROUND OF THE INVENTION

This invention relates generally to a radiosurgery system employing multiple beams of radiation focused onto a stereotactically localized target, and more particularly to stereotactic radiosurgery apparatus affording greatly improved mechanical accuracy in the focusing of radiation from a moving linear accelerator with respect to a moving stereotactic frame.

In 1951, Dr. Lars Leksell coined the term "radiosurgery", to describe the concept of focusing multiple beams of external radiation on a stereotactically localized intracranial target. After experimentation with standard X-ray treatment devices, proton beam, and linear accelerators, he and his collaborators developed a device which is called the GAMMA KNIFE (currently marketed by the Electra Corporation, Stockholm, Sweden). The device consists of a hemispheric array, currently containing 201 Cobalt-60 sources. The radiation from each of these sources is collimated and mechanically fixed, with great accuracy, on a focal point at the center of the hemisphere. When a patient has a suitable lesion for treatment (usually an intracranial arteriovenous malformation), it may be precisely localized with another device called a stereotactic frame. Using the stereotactic apparatus, the intracranial target is positioned at the focal point of the GAMMA KNIFE. Since each of the 201 radiation pathways is through a different area of the brain, the amount of radiation to normal brain tissue is minimal. At the focal point, however, a very sizable dose is delivered which can, in certain cases, lead to obliteration of the lesion. This radiosurgical treatment is, in some instances, a much safer treatment option than conventional surgical methods.

Four GAMMA KNIFE devices are currently being used worldwide for stereotactic radiosurgery (Stockholm, Sweden; Buenas Aires, Argentina; Sheffield, England; Pittsburgh, U.S.A.), and have been used to treat approximately 1500 patients. The results of treatment, as well as many technical issues, have been discussed in multiple publications. Several factors, however, have impeded the widespread usage of this device. First, the device costs about $2.2 Million Dollars, U.S. Second, the Nuclear Regulatory Commission has ruled that this device cannot be shipped loaded in the U.S.A. Consequently, loading must be done on site, necessitating the construction of a portable hot cell. Third, the half life of Cobalt-60 is 5.2 years, which requires reloading the machine, at great expense, every 5–10 years. Fourth, the dosimetry system currently marketed with the device is relatively crude, especially when utilized with more modern imaging modalities such as CT scan and MRI scan.

An alternative method for radiosurgery involves irradiation of intracranial targets with particle beams (i.e., proton or helium). In this instance, one does not rely solely on multiple cross-fired beams of radiation. A physical property of particle beams, called the "Bragg-peak effect", allows one to deliver the majority of the energy of a small number of beams (approximately 12) to a precisely predetermined depth. Multiple publications regarding particle irradiation of intracranial lesions (especially pituitary tumors and arteriovenous malformations) have appeared in the literature. The results have not generally been as good as those obtained with the GAMMA KNIFE. This may, however, be solely a consequence of patient selection criteria. Particle beam devices require the availability of a cyclotron. Only a few such high energy physics research facilities exist in the world.

A third current radiosurgical method uses a linear accelerator (LINAC) as the radiation source. As mentioned above, Leksell rejected the LINAC as mechanically inaccurate. More recently, groups from Europe have reported their methods for radiosurgery with LINAC devices. In the U.S., researchers at the Peter Bent Brigham Hospital in Boston have developed a prototype LINAC system using highly sophisticated computer techniques to optimize dosimetry. Thus far, approximately 12 patients have been treated with good results. This LINAC system, however, suffers from certain mechanical inaccuracies which have limited its use. In addition, the computer dosimetry system employed is very time consuming, rendering the treatment program inefficient.

Currently, there is great interest in radiosurgery. Although the GAMMA KNIFE represents the "gold standard", its great expense and requirement for frequent replenishment of radiation sources have discouraged most potential users. The proton beam devices are never likely to be widely available because of the requirement for high-energy particle beam source (cyclotron). The linear accelerator offers an attractive alternative to such devices. However, a major disadvantage of known linear accelerator based systems is their mechanical inaccuracy.

It is desirable to provide stereotactic radiosurgery apparatus employing linear accelerators which overcomes the disadvantages of known systems, and it is to end that the present invention is directed.

SUMMARY OF THE INVENTION

The present invention affords stereotactic radiosurgery apparatus particularly adapted for use with the LINAC which comprises a guiding structure having three bearing systems for eliminating mechanical inaccuracies occasioned by the relative movement between a LINAC gantry and a stereotactic floorstand. The three bearing systems of the guiding structure include one which guides the radiation collimator, one which allows rotation of the stereotactic floorstand, and one which allows the gantry to drive the collimator and couples the collimator of the LINAC to the stereotactic localizing device. The collimator itself is mechanically uncoupled from the LINAC housing. As the LINAC arcs through space, the mechanical bearing system ensures that "sag" in the LINAC does not result in angular deviation of the collimated beam from the target point. These bearing systems, therefore, greatly improve the mechanical accuracy of the LINAC, eliminating the major previous disadvantage of this radiosurgical method.

The invention may be employed with a dosimetry system being developed at the University of Florida which incorporates improvements in computer hardware and software that allow very rapid but highly accurate dosimetry computations. The hardware utilized includes the SUN 3/280 system, with a fast rate array processor and DIGIKON digitizing board. This configuration allows greater than 4 MIPS and 12

MEGAFLOPS. Such improvements in software design and hardware will allow dosimetry calculations in approximately one tenth of the time currently required by the Boston system, while greatly exceeding the sophistication currently obtained with the GAMMA KNIFE system. Thus, the time efficiency of the treatment process will be greatly improved.

The invention overcomes a major previous disadvantage of LINAC based systems, mechanical inaccuracy. It also offers improved dosimetry and quality control procedures. The price of LINAC based radiosurgical systems in an order of magnitude less than GAMMA KNIFE and, therefore, very attractive economically.

An additional advantage of LINAC based systems is its potential applicability to lesions elsewhere in the body (GAMMA KNIFE is currently limited by design to the head). The inventive concept of mechanically coupled LINAC systems and stereotactic localization is also useful for radiation therapy of may different types of lesions throughout the body.

Briefly, in one aspect, the invention provides radiosurgery apparatus comprising a gantry supported for rotation about a horizontal axis, the gantry carrying a radiation-emitting head for movement in an arc in a substantially vertical plane about a center point corresponding to an intersection of the horizontal axis and the vertical plane; a fixed mounting plate; a stand supported on the mounting plate by first bearing means for rotation of the stand about a vertical axis located in said vertical plane, the vertical axis intersecting said center point; a first support member connected to the mounting plate; a second support member rotatably connected to the first support member by second bearing means for rotation about said horizontal axis, the second support member having an arm adapted to be positioned adjacent said head; a collimator connected to the arm for focusing radiation at said center point; and gimbal means carried by the head for coupling the collimator to the head such that upon rotation of the gantry about the horizontal axis the collimator swings in another arc in said vertical plane while maintaining a predetermined distance between the collimator and said center point so as to compensate for deviations in the movement of the head with respect to the center point.

The present invention may alternately be described as stereotactic radiosurgery apparatus comprising a gantry supported for rotation about a gantry axis, the gantry having a radiation-emitting head for movement in a radiation plane about a center point corresponding to an intersection of the gantry axis and the radiation plane. The gantry axis is normal to the radiation plane. A collimator is disposed to focus radiation from the radiation-emitting head on the center point. A collimator linking means links movement of the collimator to the head for automatic rotation of the collimator in the radiation plane and about the gantry axis upon rotation of the gantry, the collimator linking means allowing the collimator to track rotation of the gantry with no or minimal transfer of positioning inaccuracies from the gantry to the collimator. A patient support means supports a patient for treatment. The collimator linking means is a mechanical connection between the collimator and the head automatically moving the collimator with the gantry and allowing the collimator to move relative to the gantry to minimize incorporation of positioning inaccuracies from the gantry to the collimator. A first support member, a collimator bearing means, and a second support member rotatably mounted to the first support member by way of the collimator bearing means are used. The collimator is fixed to the second support member and the first support member is anchored independently of the gantry (i.e., the first support member is not anchored to the floor or ground or other fixed base by way of the gantry). The collimator linking means is a gimbal mounted to the head. The gimbal comprises an outer member mounted to the head, and intermediate member pivotably connected to the outer member, and an inner member pivotably connected to the intermediate member. The inner member serves as a slip collar having the collimator extending therethrough. Each of the outer member, intermediate member, and inner member is a ring. The patient support means includes a treatment table for supporting the bulk of a patient and a stereotactic floorstand for supporting a portion of the patient subject to radiation from the radiation-emitting head. The treatment table and the stereotactic floorstand are both rotatable about a patient axis in the radiation plane. The stereotactic floorstand is operable to rotate the portion of the patient by way of a floorstand bearing means, the floorstand bearing means mounted to allow precise rotation of the floorstand with minimal or no incorporation of any positional inaccuracies from the treatment table. The floorstand linking means links movement of the stereotactic floorstand to the treatment table for automatic rotation of the stereotactic floorstand about the patient axis upon rotation of the treatment table about the patient axis. The floorstand linking means is a mechanical connection between the stereotactic floorstand and the treatment table. The floorstand linking means includes at least one arm fixed relative to the treatment table and extending to the stereotactic floorstand to rotate the stereotactic floorstand with the treatment table, while also allowing movement of the treatment table relative to the stereotactic floorstand.

The invention may alternately be described as a stereotactic radiosurgery apparatus comprising: a gantry supported for rotation about a gantry axis, the gantry having a radiation-emitting head for movement in an arc in a radiation plane about a center point corresponding to an intersection of the gantry axis and the radiation plane, the gantry axis being normal to the radiation plane. A collimator is disposed to focus radiation from the radiation-emitting head onto the center point. A patient support means to support a patient for treatment by the head includes a treatment table for supporting the bulk of the patient and a stereotactic floorstand for supporting a portion of the patient subject to radiation from the head. The treatment table and stereotactic floorstand are both rotatable about the patient axis in the radiation plane. The stereotactic floorstand is operable to rotate the portion of the patient by way of a floorstand bearing means. The floorstand bearing means is mounted to allow precise rotation of the floorstand with minimal or no incorporation of any positional inaccuracies from the treatment table. The stereotactic floorstand is anchored independently of the treatment table (i.e., the stereotactic floorstand is fixed to a base or floor and is not fixed to the treatment table).

BRIEF DESCRIPTION OF THE DRAWINGS

The above and other features of the present invention will be more readily understood when the following description is considered in conjunction with the accompanying drawings wherein like parts have the same number throughout and in which:

FIG. 5A is a top exploded view of parts from FIG. 5;

FIG. 8 is a perspective view illustrating conceptually a preferred form of a gimbal bearing in accordance with the invention;

FIG. 9 shows an alternate arrangement for supporting a collimator;

FIG. 10 shows an alternate arrangement for supporting a floorstand;

FIG. 11 shows a further alternative arrangement for supporting both the collimator and a floorstand by way of a common support;

FIG. 12 shows a side view of an arrangement for linking rotation of a floorstand to rotation of a treatment table;

FIG. 13 shows a cross-section view of the connection between the floorstand and treatment table of FIG. 12; and FIG. 14 shows a side view of an alternate arrangement for linking a floorstand to a table.

DETAILED DESCRIPTION

The invention is particularly well adapted for compensating for misalignments due to mechanical inaccuracies of a moving linear accelerator head in order to maintain precise focusing of the radiation at a predetermined point, and will be described in that context. As will become evident, however, this is illustrative of only one utility of the invention.

Figures 1, 2:
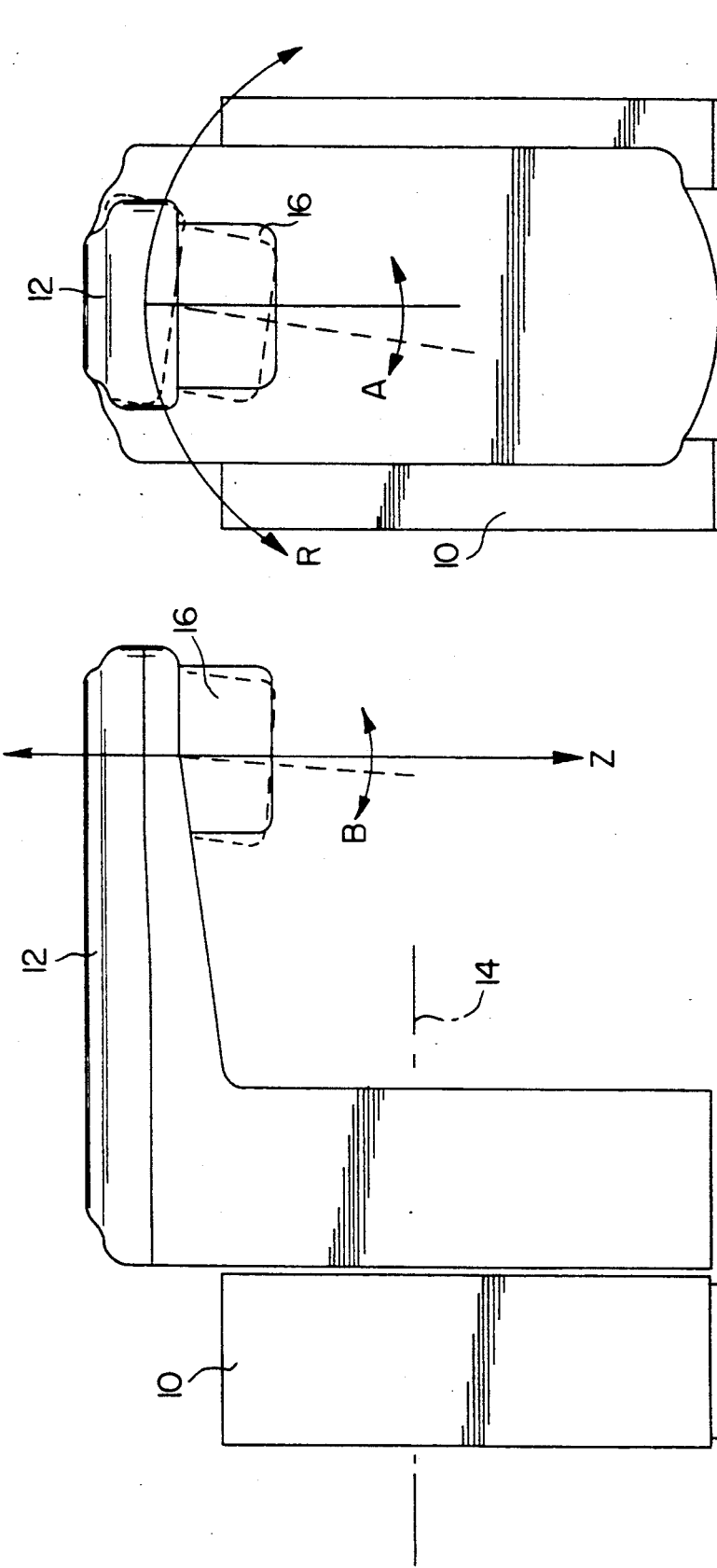
FIGS. 1 and 2 are a side elevation view and an end elevation view, respectively, of conventional linear accelerator apparatus which may be employed for stereotactic radiosurgery, the figures illustrating possible misalignments of a radiation-emitting head of the apparatus.

FIGS. 1 and 2 illustrate a conventional LINAC device which comprises a fixed base 10 and an L-shaped gantry 12 which is rotatable with respect to the base about a horizontal axis 14. The gantry carries a radiation-emitting head 16, and rotation of the gantry causes the head to sweep through an arc R located in a substantially vertical plane which is perpendicular to the horizontal axis. The dotted lines in the figures indicate potential misalignments caused by mechanical inaccuracies or sag of the gantry in any of the directions indicated in the FIGS. as A, B or z. These misalignments result in misfocusing of the radiation from the head 16 and are intolerable in radiosurgery, for the reasons noted hereinafter.

In order to best understand the invention, the three principle components of a stereotactic radiosurgery procedure will first be explained. These components are localization, dose computation and optimization, and execution of treatment. The ultimate accuracy of the procedure is dependent on each of these components.

The first component in the procedure involves the localization of the tumor. This is accomplished by one of two means. Currently, the method of choice is through stereotactic angiography. The procedure begins with the stereotactic ring being fitted to the patient. An angiographic localizing device is then attached to the ring. This device is known and consists of four sets of fiducial alignment markers. Two sets of these markers project onto each of two orthogonal angiographic x-rays. By location of the fiducial points and the target on each x-ray, the precise, x, y, z coordinates of the target (to an accuracy of 1 mm) relative to the stereotactic ring can be derived. While this part of the procedure allows the coordinates of the target relative to the localization ring to the determined, more anatomical information is needed for dosimetric analysis.

The next step replaces the angiographic localizing device with another localizer specially designed for localization in computer tomography. This is the standard BRW CT Localizer. The patient is aligned in the CT gantry and contiguous 5 mm slices, beginning at the level of the localization ring and advancing superiorly past the top of the patient's skull, are obtained. If the target volume can be identified in the computerized tomography image, then the x, y, z coordinates of the target volume are again calculated. (This can provide a double check of the x, y, z coordinates relative to the stereotactic ring.) If not, then the target obtained from the angiographic procedure can then be superimposed onto the CT scan data.

With the digitally encoded data from the CT scan and the two angiographic films, the data may be then transferred to a dosimetry computer system. The CT scan provides three dimensional anatomical information of the patient allowing a solid patient model to be constructed. The coordinates of the target volume from the angiogram and the CT scan data are then merged.

Computation and Dose Optimization: In order for the high single fractions of radiation to be delivered to the target volume, a technique to concentrate the radiation at the target while spreading out the radiation to lesser concentrations throughout the normal tissues must be utilized. Moving the radiation source through multiple arcs achieves this objective. It is important for the radiotherapist and neurosurgeon to be able to examine the consequence of each portion of the arc. The computer system which computes the dosimetry must have the ability to display each arc segment. In the routine stereotactic procedure, it is anticipated that four arcs, three at 100 degrees and one at 240 degrees, will be utilized. The computer must allow the CT scan to be reformatted in each of these arc planes (relative to the patient's skull) so that each individual arc's dose distribution can be examined. If any particular arc results in an extensive dose to a critical structure, the therapist can alter the arc parameters to avoid the anatomical area of concern. The first version of the dosimetry system under development will allow dose optimization through operator control. For subsequent versions, the operator will identify the target region and the areas where dose should be minimized. The computer will then, through use of an optimization algorithm, design the treatment which best concentrates the radiation over the tumor volume while minimizing the dose to normal tissues. The spacing between arcs, the size of the collimator, and the variation in arc length and weight will be parameters used in the optimization.

The method necessary for dose computation and optimization using a CT scan is complicated by the high resolution necessary in the procedure. The stereotactic targets can be identified to plus and minus a millimeter. The treatment portals can range anywhere from 1 to 3 cm in diameter. The spatial coordinates of the computational grid, in the area of the target, must be in the 1 mm range. However, there is little need for 1 mm accuracy outside a 5 cm radius of the target itself. A 0.5 grid is adequate in this region. By working with both the 1 mm and 5 mm grids, the number of computation points at which a dose must be evaluated for the complex arcs can be vastly reduced.

Once the acceptable treatment scheme has been derived, the coordinates of the isocenter (focal point of the radiation), the collimator size, and the arc parameters are then transferred to the operator of the linear accelerator.

Figure 3:
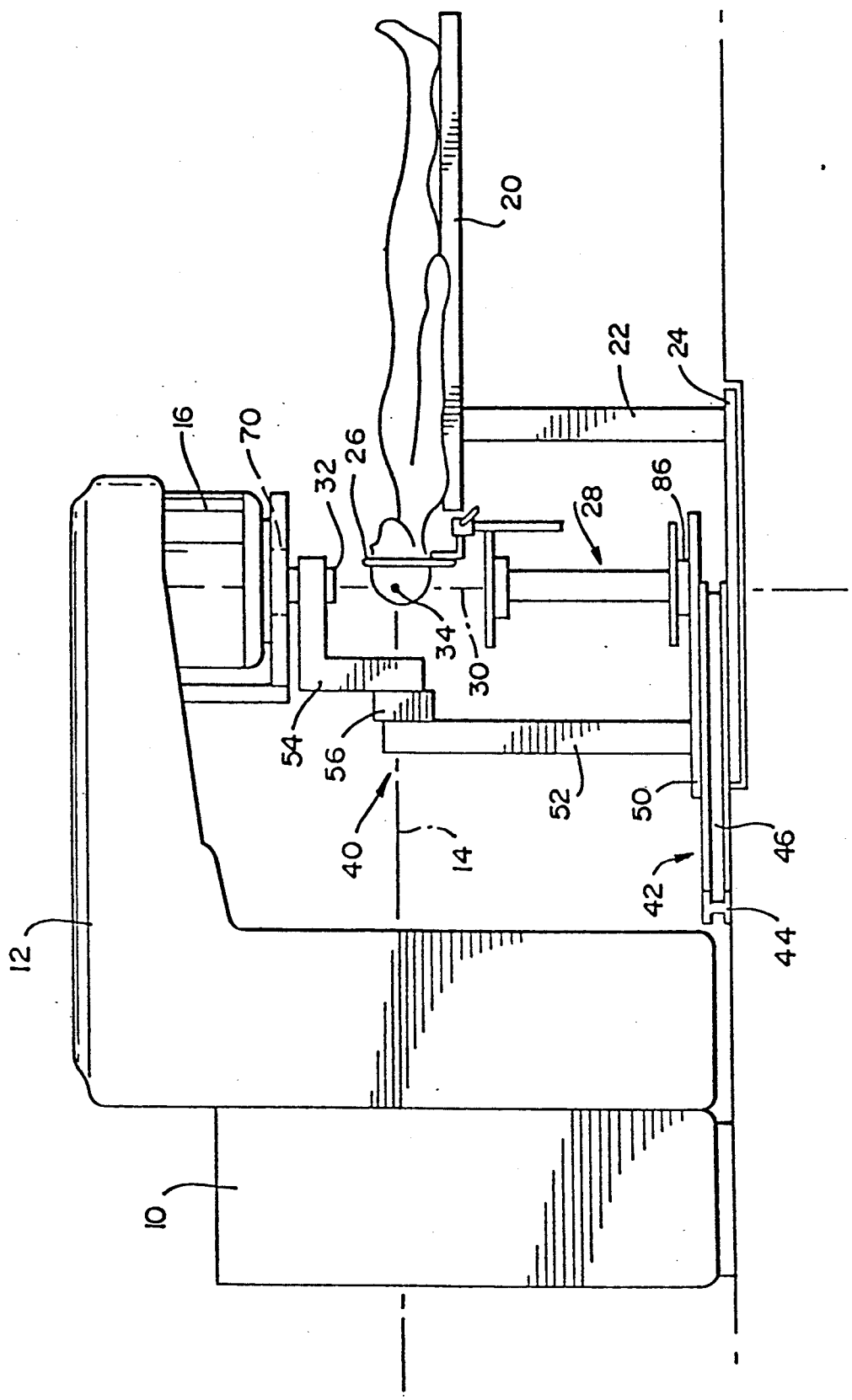
FIGS. 3 and 4 are a side elevation view and a top view, respectively, of stereotactic radiosurgery apparatus embodying the invention.
Figure 4A:
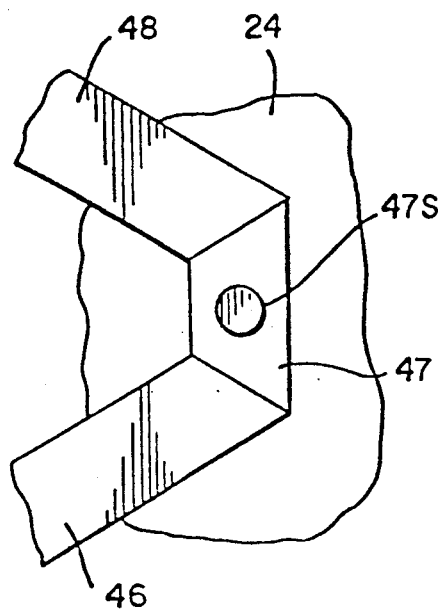
FIG. 4A is a top view showing parts of a floorstand support arrangement.
Figure 4B:
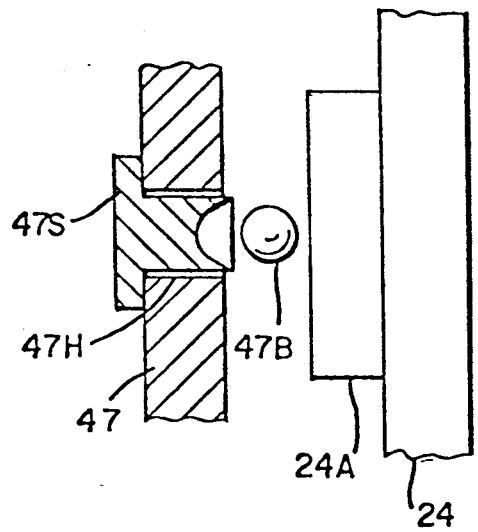
FIG. 4B shows a side exploded view with some parts in cross-section of parts of FIG. 4A.
Figure 4:
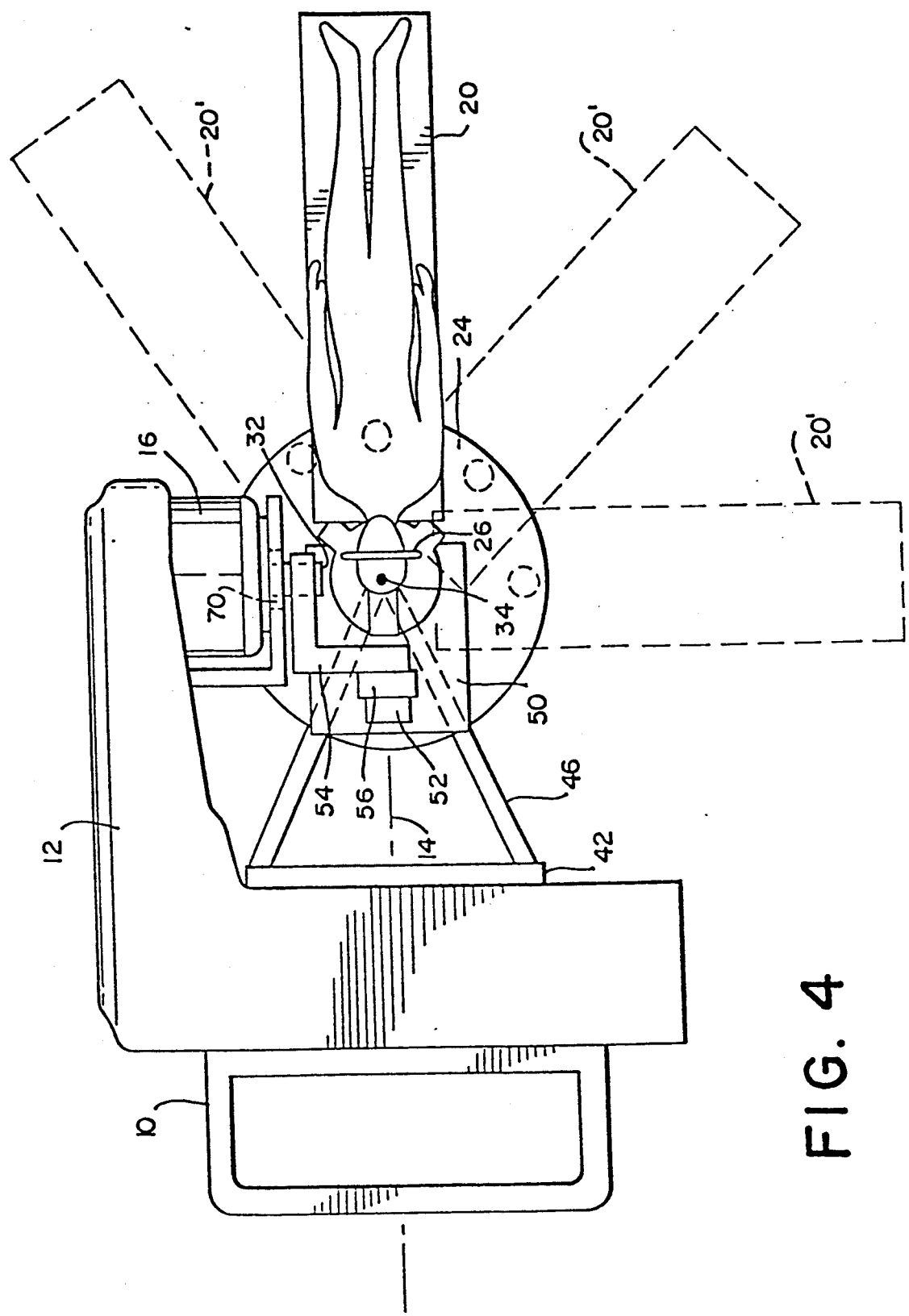

FIGS. 3 and 4 illustrate the stereotactic treatment setup. As shown, a patient is placed on a treatment table 20 which is supported by a member 22 on a rotating plate 24 positioned in the floor. The patient's head is immobilized by a stereotactic ring 26 which is connected to a BRW stereotactic floorstand 28 which has been modified in accordance with the invention (as will be explained shortly) so that the patient's head is at a predetermined location with respect to the radiation-emitting head 16 of the LINAC. As shown in FIG. 4, rotating plate 24 may be rotated to position the table at different locations 20'' as indicated by the dotted lines. Gantry 12 of the LINAC may be rotated about base 10 to swing treatment head 16 in an arc located in a vertical plane indicated by the dotted line 30 in FIG. 3. The radiation from head 16 is collimated by a collimator 32 and is confined to the vertical plane 30 in which the treatment head moves. FIG. 4 shows the gantry 12 swung over to one side such that the radiation enters the left side of the patient's head, and FIG. 3 shows the gantry in an upright position such that the radiation enters through the forehead of the patient. Collimator 32 focuses the radiation at an isocenter or center point 34 corresponding to the intersection of the horizontal axis 14 of rotation of the gantry and vertical plane 30. Center point 34 corresponds to the origin of the arc through which the treatment head 16 swings. Rotating plate 24 rotates about a vertical axis which coincides with vertical plane 30. Accordingly, as gantry 12 is swung through an arc the radiation of head 16 passes through different portions of the patient's head and is concentrated at center point 34 for all rotational positions of rotating plate 24.

Prior to treatment of the patient, a test treatment procedure is first run. A phantom pointer allows placement of a stainless steel ball as a phantom target on the modified stereotactic floorstand 28 in accordance with a known test procedure and an appropriate collimator placed into the stereotactic dose delivery apparatus (radiation-emitting head 16). A trial arc is then made to assess the mechanical precision and accuracy of placement of the moving treatment head, and the overall accuracy of the location procedure is tested using radiation and x-ray film in known fashion. If this is successful, patient treatment is executed.

As previously noted, mechanical inaccuracies and sag in the gantry as it is rotated through its arc can cause deviations from the nominal origin of the arc (center of rotation) and, thus, deviations in the focal point of the radiation from the desired center point 34. Attempting to deliver a dose of radiation to a spherical volume with an accuracy of plus or minus 1 mm requires that the LINAC have tolerances which are much more stringent than that. Conventional LINAC's have a gantry isocentric accuracy of 2 mm, and patient support rotation has an accuracy of 2 mm. It is therefore possible for a target placed at the isocenter 34 to find itself 4 mm from the center of the radiation beam after gantry and table rotation. This is clearly unacceptable. If small treatment targets are to be attempted, these potential isocentric inaccuracies must be eliminated. The invention accomplishes this by employing a guiding and stabilizing structure 40 which rotates in the vertical plane 30 of the gantry rotation and confines the movement of collimator 32 to a precise arc with no more than 0.1 mm misalignment. Moreover, the invention reduces the rotational inaccuracy of the treatment table to a maximum misalignment of 0.1 mm, as will be described shortly. By reducing the allowable treatment table and gantry misalignments by a factor of 10 from the normal inaccuracies, the invention enables a dose of radiation to be delivered to a target within plus or minus 1 mm. The guiding and support structure 40 and the stereotactic floorstand 28 of the invention which accomplish this are shown in FIGS. 3 and 4 and in somewhat more detail in FIGS. 5 and 6.

Referring to these figures, the invention employs an A-frame supporting structure 42 which may be constructed of H-beams. One beam, such as 44 may be connected to the floor adjacent to the gantry such that the two arms 46 and 48 extend over rotating plate 24 (See FIG. 3) and are spaced therefrom to enable the plate to rotate. A generally rectangular plate 50, as of aluminum, may be supported on the frame as shown. Plate 50 supports the rotating and guiding structure 40 and the floorstand 28.

As shown in FIG. 4A and FIG. 4B, arms 46 and 48 are connected by member 47, disposed below plate 50 (plate 50 not shown in FIGS. 4A and 4B). To prevent the plate 50 and floorstand mounted thereon from sagging from the cantilever extensions of arms 46 and 48, the plate 50 is supported by bearing 47B which is captured between screw 47S and plate 24A which is fixed to plate 24. As plate 24 moves, bearing 47B allows such movement but supports the plate 50.

As shown in the FIGS., the guiding and supporting structure 40 may comprise a first substantially vertical support member connected to plate 50, and a second angled support member 54 rotatably connected to the upper end of support member 52 by a main arcing bearing 56 such that the center of rotation of support member 54 coincides with horizontal axis 14 about which the gantry rotates. The main arcing bearing 56 comprises a high precision bearing, which may take the form illustrated in FIG. 7. As shown, the bearing may comprise a first fixed plate 60, as of steel, which rotatably supports a center plate 62 having a hub 64. Center plate 62 is captured in three orthogonal directions by rolling bearings 66 and is machined to a flatness and concentric accuracy which allows no more than 0.03 mm in variation as it rotates. Plate 60 may be connected to the vertical support member 52, and hub 64 may be connected to support member 54.

Figure 5:
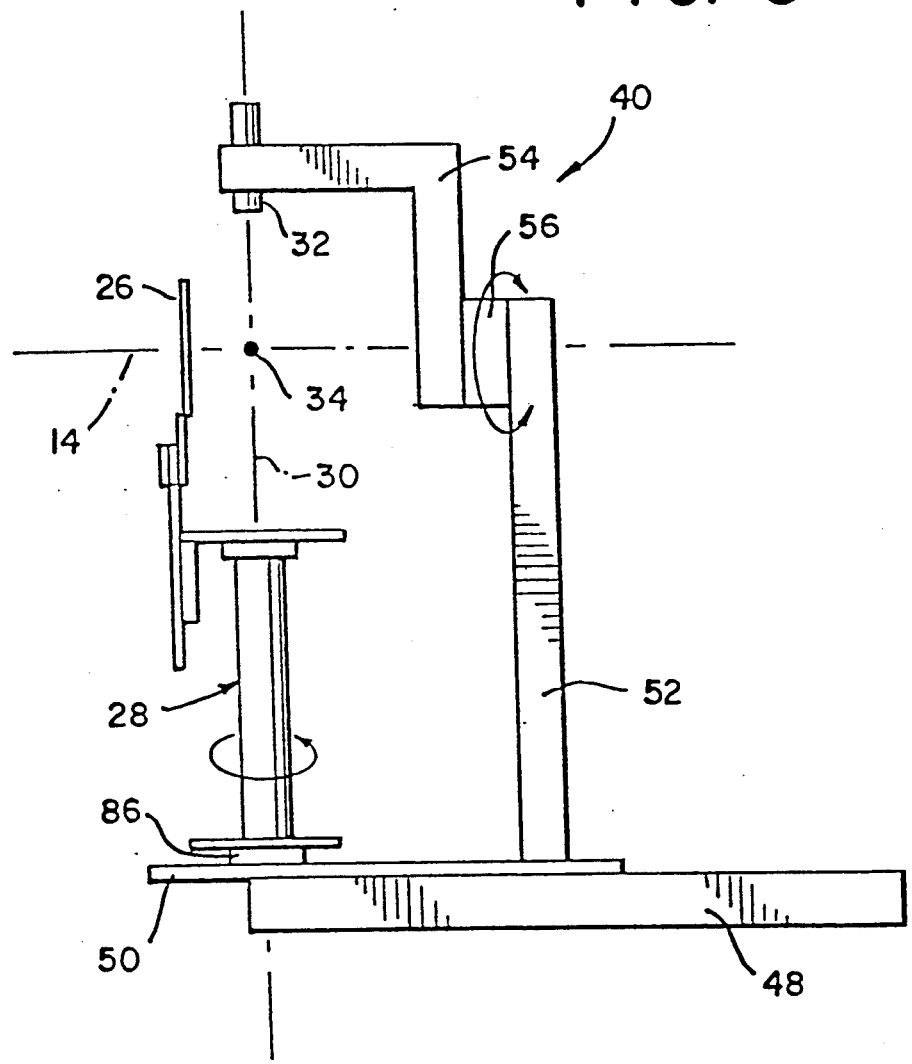
FIGS. 5 and 6 are a side elevation view and a top view, respectively, of guiding structure in accordance with the invention.
Figure 6:
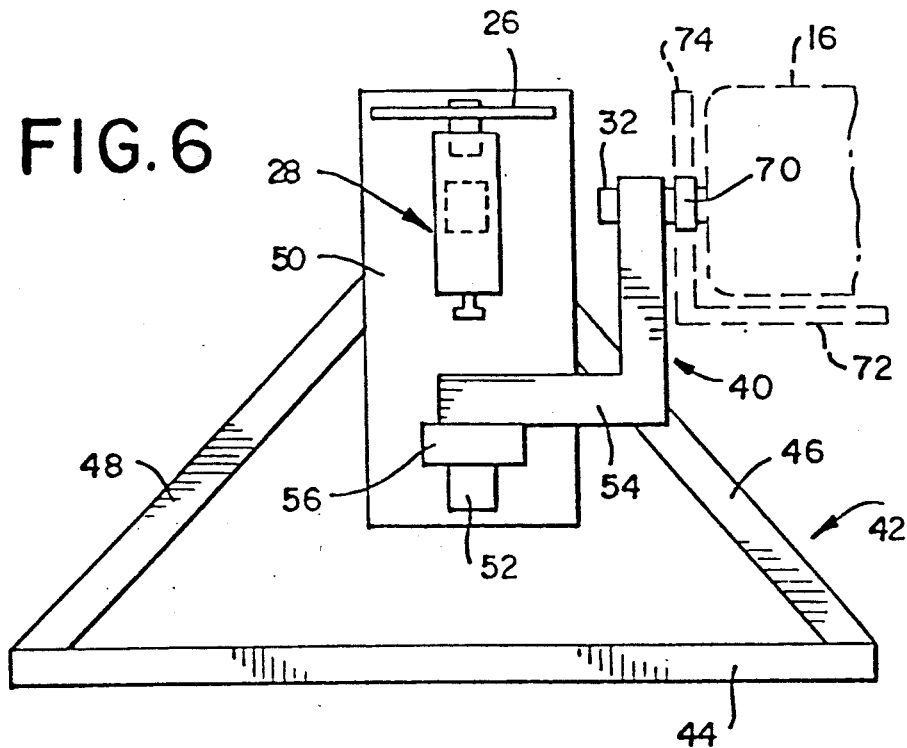

As shown in the FIGS., collimator 32 is connected to the horizontal (in FIGS. 3 and 5) arm of support member 54. As shown in FIG. 5A, member 54 may include two pieces 54F and 54S with complimentary holes to clamp collimator 32 when bolted together by bolt 54B extending through hole 54H. Collimator 32, in turn, may be coupled to head 16 of the LINAC through the use of a gimbal-type bearing 70, such as shown in FIG. 8. As shown in FIG. 8, the gimbal bearing may comprise an outer ring 76, an intermediate ring 78 pivotally connected to the outer ring, and an inner ring 80 pivotally connected to the intermediate ring 78. Ring 80 constitutes a slip collar which snugly and slidingly receives the collimator 32.

Figure 3A:
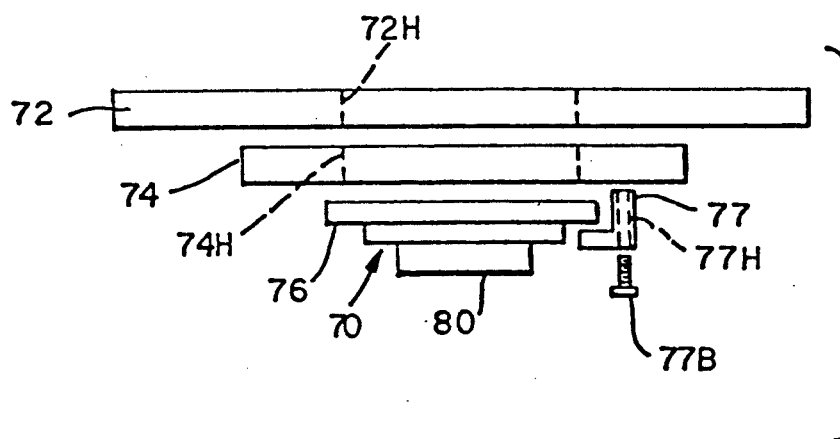
FIG. 3A is a side exploded view of a linking arrangement for linking a collimator to a radiation-emitting head.

With reference to FIG. 3A, gimbal 70 would be clamped to plate 74 by several circumferentially spaced L-shaped members 77 (only one shown) with bolt 77B extending through hole 77H into a hole (not shown) in plate 74. Plate 74, which has a circular hole 74H, is positioned relative to plate 72 by positioning pins (not shown) on plate 74 cooperating with positioning holes (not shown) on plate 72 and is bolted (bolts now shown) to plate 72. Plate 72 has hole 72H which, like hole 74H, allows it to accommodate a collimator (not shown in FIG. 3A) placed within ring 80. The plate 72 would be mounted to the radiation head by positioning pins and holes and bolts. The collimator slip ring 80 could be moved slightly by loosening the members 77 and re-tightening them after gimbal 70 and its ring 80 are repositioned. The ring 80 serves as a linking member to link movement of the collimator 32 to the radiation head 16.

As gantry 12 rotates, support and guiding structure 40 serves to guide the collimator through a very precise and accurate arc having a center of rotation at center point 34. Gimbal bearing 70 allows the head of the LINAC to pull the collimator through the arc as the gantry rotates, but removes all torques on the collimator. Thus, any misalignments or sag of the gantry in any direction will not be transmitted to the collimator and will not result in any forces on it. Thus, support and guiding structure 40 compensates for any misalignments in the rotation of the gantry by ensuring that the movement of the collimator 32 is precisely controlled. As a result, the radiation from head 16 is precisely focused at center point 34.

An alternative to gimbal 70 could be a ball and socket (not shown) with the socket secured to the radiation head 16 and the ball having a cylindrical hole to accommodate the collimator in slip ring fashion and avoid putting torque on the collimator.

Figure 7:
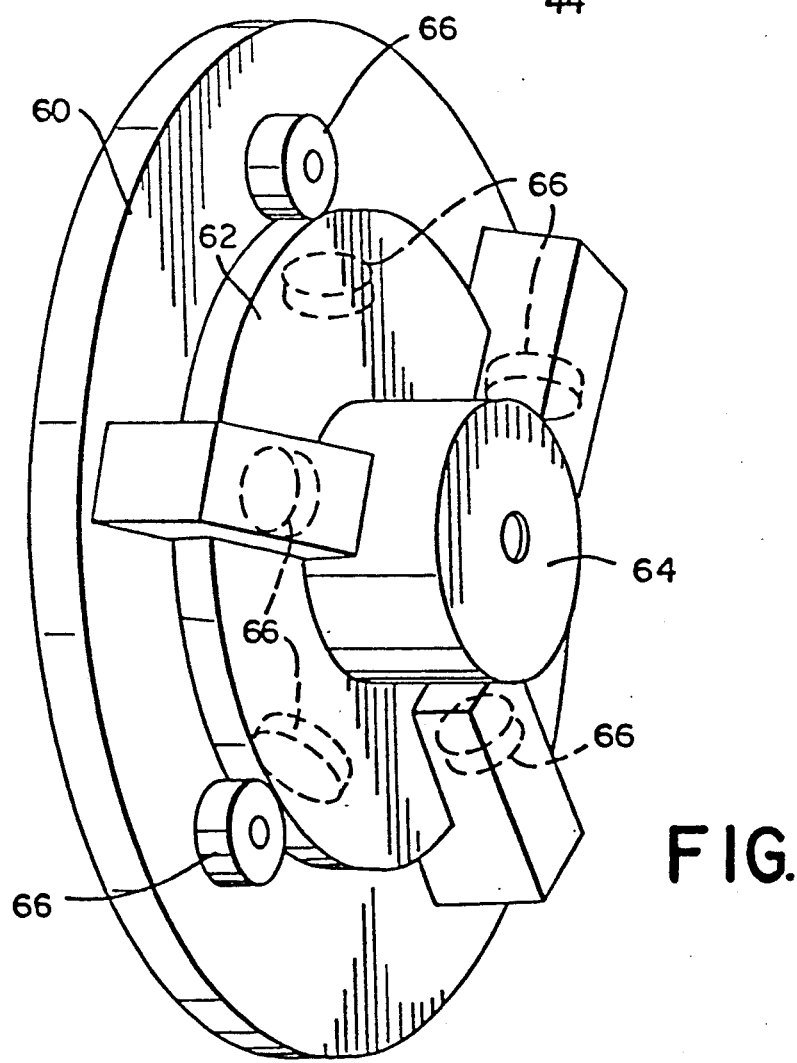
FIG. 7 is a perspective view illustrating conceptually a preferred form of a main arcing bearing in accordance with the invention.

Floorstand 28 is also rotatably mounted on plate 50 by a bearing 86, which may be similar to the main arcing bearing of FIG. 7. The floorstand is precisely located such that its axis of rotation is vertical and lies in plane 30. The axis of rotation of the floorstand intersects center point 34. Bearing 86 of the floorstand is also machined and concentric accuracy which allows no more than 0.03 mm in variation as it rotates. Accordingly, the floorstand compensates for any rotational inaccuracies in rotating plate 24 and ensures that the treatment point in the patient's head precisely coincides with isocenter 34 for all rotational positions of the table. Unlike prior floorstands which have been directly mounted to a plate such as 24, the use of bearing 86 allows floorstand 28 to avoid inaccuracies from the rotation of plate 24. Floorstand 28 is independently anchored from table 20 (i.e., floorstand 28 is not fixed relative to table 20 and plate 24).

Once alignment of the guiding and support structure 40 and the rotating floorstand 28 with respect to plate 50 have been achieved, all components are doweled and pinned in position to maintain the alignment. The floorplate may then be mounted on the H-beam structure. This arrangement provides a mounting system which can be easily fitted and removed from the LINAC such that when the LINAC is not being used for a stereotactic procedure, the LINAC is returned to its unmodified state.

With reference now to FIG. 9, an alternate arrangement for mounting a collimator is shown. For ease of illustration, the simplified side view of FIG. 9 only includes elements which are different from the structures previously discussed with respect to FIGS. 3-8. The components of the structure of FIG. 9 are labeled in the 100 series with the same last two digits as the corresponding component, if any, of the previously discussed embodiment. A support member 152 is fixed to a plate 150 and is used to maintain the accuracy of rotation of collimator 132 about a gantry axis 114 (which axis is horizontal for the preferred embodiment). The collimator 132 functions in the same way as the previously discussed collimator 32 and would be coupled to a radiation head such as 16 of FIG. 3 by way of a mechanical linking means such as the gimbal structure previously discussed with respect to FIG. 3. However, since the linkage between the collimator 132 and such a radiation head would be identical to that shown in FIG. 3 and the related and earlier discussed FIGS., these features are not shown in FIG. 9. FIG. 9 is different than the previously discussed first embodiment in that the collimator 132 is mounted to the support member 152 by way of a support member 154 using an internal taper bearing 156 as opposed to the external type bearing 56 in the earlier discussed embodiment. Such taper bearings are well known and need not be discussed in detail, but it should briefly be noted that they are known bearing structures capable of very precise bearing arrangements.

FIG. 10 shows an alternate floorstand 128 (which might also be used with the structure of FIG. 9). The floorstand 128 has a fixed base 190 with a fixed shaft or member 192 extending up therefrom. A bearing system 186 allows rotation of a rotatable shaft 194 relative to the fixed shaft 192. A platform 196 is mounted on the top of the shaft 194 and a stereotactic ring 126 is mounted thereon. As with the earlier embodiment, the axis of rotation corresponding to the central axis of shaft 194 would be coaxial to the axis of rotation of a treatment table such as 20 of FIG. 3 and FIG. 4. This axis of rotation corresponding to the central axis of shaft 194 might be considered as a patient axis since the patient rotates about that axis upon movement of the treatment table 20 and rotation of the rotatable part of floorstand 128.

FIG. 11 shows an alternate construction wherein the precision bearing arrangement for a collimator 232 and a floorstand 228 are commonly mounted to a fixed member 298. The member 298, only a portion of which is shown, would be fixed to a base (not shown) in similar fashion to the fixing of member 52 in FIG. 3. Extending up from member 298 is a member or portion 252 which is rotatably connected to the collimator 232 by way of a support arm 254 and an internal taper bearing 256. A portion or member 292 connects a tapered bearing 286 to the floorstand 228 including platform 296 and stereotactic ring 226. The arrangement of FIG. 11 provides for highly precise rotation of a patient's head or other bodily part by way of the stereotactic floorstand portion 228 and highly accurate rotation of the collimator 232. The use of the precision tapered bearings 256 and 286 and the other elements of the structure of FIG. 11 would of course be used in connection with a treatment table and radiation-emitting head and other structures as shown in FIG. 3. For ease of illustration, FIG. 11, as well as the FIGS. 9 and 10, do not show portions of the system which are identical to the structures of FIGS. 3-8. In other words, the collimator 232 would be linked to the radiation head by way of a gimbal arrangement as previously discussed and the floorstand 228 would rotate in connection with rotation of a table 20 and about a common axis with such a table as discussed above with respect to FIGS. 3-8.

With reference now to FIG. 12, an arrangement for linking the movement between the treatment table 20 and the floorstand 28 will be shown. The structure of FIG. 12 would be identical to that shown previously with respect to FIG. 3-8 and only a portion is shown in FIG. 12 for convenience. Additionally however, FIG. 12 includes a linking means 300. As shown in FIG. 12 the linking means 300 is a mechanical structure including an arm 302 extending from the member 322 to a member 304 corresponding to the shaft of floorstand 328.

Considering FIG. 12 in conjunction with FIG. 13, the structure of floorstand linking means 300 is shown to include two of the arms 302 which are welded or otherwise fixed to a locking collar 308 using a bolt 310 to lock around the shaft 22 corresponding to the treatment table 20. The collar 308 might be hinged opposite bolt 310 or alternately could simply be compressed against its resilience by tightening bolt 310. The two arms 302 extend out and grip the member 304 which extends up as part of the stereotactic floorstand 328. Two pressure pads 306 grip the member 304 such that the member 304 rotates by way of bearings 86 upon rotation of the table 320. However, because of the linkage by way of the pressure pads 306, the precision bearings 86 provide very precise positioning of the floorstand 328 while minimizing any transmission of inaccuracies from the treatment table 320. The pressure pads 306 allow slight relative movements between the treatment table 320 and the floorstand 28.

FIG. 14 shows an alternate linking arrangement 400 which might be used to link rotation of a treatment table 420 having a toe bearing system. The linking means 400 includes a vertical shaft 410 which might be a single shaft or two parallel members such as the arms 302 in FIG. 13. In either case, the member 410 is fixed at its lower end to a plate which rotates with the table 420. The linkage arrangement 400 includes two arms 402 (only one of which is visible in FIG. 14). The two arms 402 are parallel and would have pressure pads similar to those shown at 306 of FIG. 13 such that the shaft 490 of floorstand 428 would rotate upon rotation of the table 420, but quite importantly would not incorporate the positional inaccuracies of the rotation of table 420.

It will be readily appreciated that the mechanical linking means 300 and 400 of FIGS. 12-14 could be used to link rotation of the floorstands shown in FIGS. 10 and 11 to rotation of a corresponding table.

Another significant advantage of the invention is that aside from the increased isocentric accuracy which it provides, it enables independent evaluation of each of the various degrees of freedom of movement required for the procedure. The rotation of the floorstand can be separately evaluated from the guiding and support structure of the collimator, and, similarly, the movements of the guiding and support structure may be separately evaluated from those of the floorstand. Moreover, the alignment of the gimbal bearing system can be evaluated separately from the movement of either of the other two rotational bearing systems. This affords a simpler and more efficient quality control of the entire system, and easily accommodates other radiographic verifications which may be required.

While the foregoing has described a preferred embodiment of the system, it will be appreciated by those skilled in the art that variations may be made without departing from the principles and spirit of the invention, the scope of which is defined in the appended claims.

What is claimed is:

1. Stereotactic radiosurgery apparatus comprising:
   a gantry supported for rotation about a gantry axis, the gantry having a radiation-emitting head for movement in an arc in a radiation plane about a center point corresponding to an intersection of the gantry axis and the radiation plane, said gantry axis being normal to said radiation plane;
   a collimator disposed to focus radiation from said radiation-emitting head on said center point; and
   collimator linking means for linking movement of said collimator to said radiation-emitting head for automatic rotation of said collimator in said radiation plane and about said gantry axis upon rotation of said gantry, and wherein said collimator linking means allows movement of said collimator relative to said radiation emitting head, said collimator linking means includes a linking member connected to said collimator, said linking member allowing said collimator to track rotation of said gantry with no or minimal transfer of positioning inaccuracies from said gantry to said collimator.

2. The stereotactic radiosurgery apparatus of claim 1 further comprising patient support means to support a patient for treatment by said radiation-emitting head.

3. The stereotactic radiosurgery apparatus of claim 1 wherein said collimator linking means is a mechanical connection between said collimator and said radiation-emitting head automatically moving said collimator with said gantry and allowing said collimator to move relative to said gantry to minimize incorporation of positioning inaccuracies from said gantry to said collimator.

4. The stereotactic radiosurgery apparatus of claim 3 further comprising a first support member, a collimator bearing means, a second support member rotatably mounted to said first support member by way of said collimator bearing means, and wherein said collimator is fixed to said second support member and said first support member is anchored independent of said gantry.

5. The stereotactic radiosurgery apparatus of claim 4 wherein said collimator linking means is a gimbal mounted to said radiation-emitting head.

6. The stereotactic radiosurgery apparatus of claim 5 wherein said gimbal comprises an outer member mounted to said radiation-emitting head, an intermediate member pivotably connected to the outer member, and said linking member, said linking member being an inner member pivotably connected to said intermediate member, said inner member serving as a slip collar and having said collimator extending therethrough.

7. The stereotactic radiosurgery apparatus of claim 6 wherein each of said outer members, intermediate member and inner member is a ring.

8. The stereotactic radiosurgery apparatus of claim 4 further comprising:

patient support means to support a patient for treatment by said radiation-emitting head, said patient support means including a treatment table for supporting the bulk of a patient and a stereotactic floorstand for supporting a portion of the patient subject to radiation from said radiation-emitting head, said treatment table and said stereotactic floorstand both rotatable about a patient axis in said radiation plane, said stereotactic floorstand operable to rotate said patient by way of a floorstand bearing means, said floorstand bearing means mounted for precise rotation of said floorstand with minimal or no incorporation of any positional inaccuracies from said treatment table.

9. The stereotactic radiosurgery apparatus of claim 8 further comprising floorstand linking means for linking movement of said stereotactic floorstand to said treatment table for automatic rotation of said stereotactic floorstand about said patient axis upon rotation of said treatment table about said patient axis.

10. The stereotactic radiosurgery apparatus of claim 9 wherein said floorstand linking means is a mechanical connection between said stereotactic floorstand and said treatment table.

11. The stereotactic radiosurgery apparatus of claim 10 wherein said floorstand linking means includes at least one arm fixed relative to said treatment table and extending to said stereotactic floorstand to rotate said stereotactic floorstand with said treatment table, while also allowing movement of said treatment table relative to said stereotactic floorstand.

12. The stereotactic radiosurgery apparatus of claim 1 further comprising:

patient support means to support a patient for treatment by said radiation-emitting head, said patient support means including a treatment table for supporting the bulk of a patient and a stereotactic floorstand for supporting a portion of the patient subject to radiation from said radiation-emitting head, said treatment table and said stereotactic floorstand both rotatable about a patient axis in said radiation plane, said stereotactic floorstand operable to rotate said patient by way of a floorstand bearing means, said floorstand bearing means mounted for precise rotation of said floorstand with minimal or no incorporation of any positional inaccuracies from said treatment table.

13. The stereotactic radiosurgery apparatus of claim 12 further comprising floorstand linking means for linking movement of said stereotactic floorstand to said treatment table for automatic rotation of said stereotactic floorstand about said patient axis upon rotation of said treatment table about said patient axis.

14. Stereotactic radiosurgery apparatus comprising:

a gantry supported for rotation about a gantry axis, the gantry having a radiation-emitting head for movement in an arc in a radiation plane about a center point corresponding to an intersection of the gantry axis and the radiation plane, said gantry axis being normal to said radiation plane; a collimator disposed to focus radiation from said radiation-emitting head on said center point; and patient support means to support a patient for treatment by said radiation-emitting head, said patient support means including a treatment table for supporting the bulk of a patient and a stereotactic floorstand for supporting a portion of the patient subject to radiation from said radiation-emitting head, said treatment table and said stereotactic floorstand both rotatable about a common patient axis in said radiation plane, said stereotactic floorstand operable to rotate said patient by way of a floorstand bearing means, said floorstand bearing means mounted to allow precise rotation of said floorstand with minimal or no incorporation of any positional inaccuracies from said treatment table and to allow movement of said floorstand relative to said treatment table, and wherein said stereotactic floorstand is anchored independently of said treatment table.

15. The stereotactic radiosurgery apparatus of claim 14 further comprising floorstand linking means for linking movement of said stereotactic floorstand to said treatment table for automatic rotation of said stereotactic floorstand about said patient axis upon rotation of said treatment table about said patient axis.

16. The stereotactic radiosurgery apparatus of claim 15 wherein said floorstand linking means is a mechanical connection between said stereotactic floorstand and said treatment table.

17. The stereotactic radiosurgery apparatus of claim 16 wherein said floorstand linking means includes at least one arm fixed relative to said treatment table and extending to said stereotactic floorstand to rotate said stereotactic floorstand with said treatment table, while also allowing movement of said treatment table relative to said stereotactic floorstand.

18. The stereotactic radiosurgery apparatus of claim 15 further comprising:

collimator linking means for linking movement of said collimator to said radiation-emitting head for automatic rotation of gantry axis upon rotation of said gantry, said linking means allowing said collimator to track rotation of said gantry with no or minimal transfer of positioning inaccuracies from said gantry to said collimator.

19. The stereotactic radiosurgery apparatus of claim 18 wherein said collimator linking means is a mechanical connection between said collimator and said radiation-emitting head automatically moving said collimator with said gantry and allowing said collimator to move relative to said gantry to minimize incorporation of positioning inaccuracies from said gantry to said collimator.

* * * * *